(12) United States Patent
Cole et al.

(10) Patent No.: US 7,824,863 B2
(45) Date of Patent: Nov. 2, 2010

(54) NUCLEIC ACID LABELING METHODS

(75) Inventors: Kyle B. Cole, Stanford, CA (US); Vivi Truong, Mountain View, CA (US); Glenn H. McGall, Palo Alto, CA (US); Anthony D. Barone, San Jose, CA (US)

(73) Assignee: Affymetrix, Inc., Santa Clara, CA (US)

( * ) Notice: Subject to any disclaimer, the term of this patent is extended or adjusted under 35 U.S.C. 154(b) by 29 days.

(21) Appl. No.: 12/256,256

(22) Filed: Oct. 22, 2008

(65) Prior Publication Data

US 2009/0054258 A1      Feb. 26, 2009

Related U.S. Application Data

(60) Division of application No. 10/983,046, filed on Nov. 4, 2004, now Pat. No. 7,504,215, which is a continuation-in-part of application No. 10/617,992, filed on Jul. 11, 2003, now abandoned.

(60) Provisional application No. 60/395,580, filed on Jul. 12, 2002.

(51) Int. Cl.
    C12Q 1/68      (2006.01)
    C12P 19/34     (2006.01)
    C07H 15/00     (2006.01)
    C07H 21/00     (2006.01)
    C07H 19/04     (2006.01)

(52) U.S. Cl. .................... 435/6; 435/91.1; 435/91.2; 536/4.1; 536/25.32; 536/26.6

(58) Field of Classification Search .............. 435/6, 435/91.1, 91.2; 536/4.1, 25.32, 26.6
    See application file for complete search history.

(56) References Cited

U.S. PATENT DOCUMENTS 5,241,060 A    8/1993   Engelhardt
6,344,316 B1   2/2002   Lockhart

FOREIGN PATENT DOCUMENTS

JP      05 331185 A     12/2001
WO      WO 01/04265     1/2001

OTHER PUBLICATIONS

Armstrong, S.A., et al, "MLL Translocations Specify a Distinct Gene Expression Profile the Distinguishes a Unique Leukemia," Nature Genetics 2002, 30:41-47.

(Continued)

*Primary Examiner*—Jezia Riley
(74) *Attorney, Agent, or Firm*—Sandra E. Wells

(57) ABSTRACT

In one aspect of the invention, a method is provided for end-labeling RNA (total RNA, mRNA, cRNA or fragmented RNA). In one aspect of the present invention, T4 RNA ligase is used to attach a 3'-labeled AMP or CMP donor to an RNA acceptor molecule. In another embodiment, a pyrophosphate molecule 3'-AppN-3'-linker-detectable moiety is used as donor molecule.

In another aspect of the present invention, a method of detecting the presence of an RNA of interest in a sample is provided, the method having the following steps: providing the sample comprising RNA which may or may not have said RNA of interest; treating the sample with a fragmenting reagent to provide RNA fragments; removing phosphate groups from said fragments to provide fragments with free 3' OH groups; ligating said fragment with a labeling reagent according to the instant invention; providing a nucleic acid array having probes directed to said RNA of interest; hybridizing the labeled nucleic acid fragments to said nucleic acid array; and determining the extent of hybridization to said probes to determine the presence of said RNA of interest.

16 Claims, 1 Drawing Sheet

OTHER PUBLICATIONS

Atencia, E.A., et al, "T4 RNA Ligase Catalyzes the Synthesis of Dinucleoside Polyphosphates," European Journal of Biochemistry 1999, 261:802-811.

England, T.E., et al.,"3'-Terminal Labelling of RNA with T4 RNA Ligase," Nature 1978, 275:560-561.

Golub, T.R., et al, "Molecular Classification of Cancer: Class Discovery and Class Prediction by Gene Expression Monitoring," Science 1999, 286: 531-537.

Harrison, B., et al, "Polymer-Stimulated Ligation: Enhanced Ligation of Oligo-and Polynucleotides by T4 RNA Ligase in Polymer Solutions," Nucleic Acids Research (Online) 1984, 12:8235-8251.

Hoffman, P.U., et al, "Synthesis and Reactivity of Intermediates Formed in the T4 RNA Ligase Reaction," Nucleic Acids Research (Online) 1987, 15: 5289-5303.

McLaughlin, L.W., et al, "Donor Activation in the T4 RNA Ligase Reaction," Biochemistry 1985, 24:pp. 267-273.

Silber, R., et al., "Purification and Properties of Bacteriophage T4-Induced RNA Ligase," Proceedings of the National Academy of Science of the U.S.A., 1972, 69: 3009-3013.

Tessier, D.C., et al, "Ligation of Single Stranded Oligodeoxyribonucleotides by T4 RNA Ligase," Analytical Biochemistry 1986, 158:171-178.

Uhlenbeck, O.C., et al, "Equimolar Addition of Oligoribonucleotides with T4 RNA Ligase," Nucleic Acids Research (Online) 1977, 4: 85-98.

Bonora G. M., et al; "Synthesis and Characterization of High-Molecular Mass Polyethylene Glycol-Conjugated Oligonucleotides"; Bioconjugate Chemistry, ACS, Washington, DC, US; vol. 8; 1997; pp. 793-797.

Cole et al, "Direct labeling of RNA with multiple biotins allows sensitive expression profiling of acute leukemia class predictor genes"; Nucleic Acid Research 2004; vol. 32; No. 11.

England, et al., "Enzymatic Oligoribonucleotide Synthesis with T4 RNA Ligase"; American Chemical Society; vol. 17, No. 11; 1978. pp. 2069-2076.

England, et al; "Specific Labeling of 3' Termini of RNA with T4 RNA Ligase"; Methods of Enzymology, vol. 65, 1980. pp. 65-74.

Hetch, et al; "Chemical Aminoacylation of tRNA's"; The Journal of Biological Chemistry; vol. 253, No. 13; issued of Jul. 10, pp. 4517-4520. (1978).

Igloi; "Nonradioactive Labeling of RNA"; Analytical Biochemistry 233, 124-129 (1996). Article No. 0016.

Kaufman, et al, "T4 RNA Ligase: Substrate Chain Length Requirements"; FEBS Letters; vol. 46, No. 1; Sep. 1974.

Richardson, et al., "Biotin and fluorescent labeling of RNA using T4 RNA ligase"; Nucleic Acids Research, vol. 11, No. 18 (1983).

Romaniuk, et al; "The effect of acceptor oligoribonucleotide sequence on the T4 RNA ligase reaction"; Eur. J. Biochem 125, 639-643 (1982).

Supplementary European search report for European Application 03764653.6 of Apr. 29, 2008.

NUCLEIC ACID LABELING METHODS

RELATED APPLICATIONS

This application is a divisional of U.S. patent application Ser. No. 10/983,046, filed Nov. 4, 2004, which is a continuation-in-part of U.S. patent application Ser. No. 10/617,992, filed Jul. 11, 2003, which application claims the benefit of U.S. provisional application 60/395,580, filed Jul. 12, 2002, the disclosures of these applications are incorporated herein by reference in their entirety for all purposes.

FIELD OF THE INVENTION

This invention relates to nucleic acid labeling compounds. These labeling compounds have a detectable moiety or moieties, which is a molecule or complex allowing for the RNA or fragment bearing it to be perceived with the appropriate equipment or test. More specifically, the invention relates to nucleic acid labeling compounds which can be used to label the 3' end of an RNA molecule or fragment. The nucleic acid labeling compounds of the instant invention can be joined to RNA through use of enzymes called RNA ligases. Such labeling is said to be direct to distinguish it from other procedures requiring conversion of the RNA into DNA. This invention also relates to the analysis of labeled RNAs using a nucleic acid microarray.

BACKGROUND OF THE INVENTION

Gene expression in diseased and healthy cells and in cells in different stages of development is oftentimes different and characterizable. The ability to monitor gene expression in such cases provides researchers and medical professionals with a powerful diagnostic tool.

One can monitor gene expression, for example, by measuring the presence or absence of a nucleic acid (e.g., a mRNA) that is the transcription product of a gene of interest. Monitoring the nucleic acid may be accomplished by chemically or biochemically labeling the mRNA with a detectable moiety followed by hybridization to a nucleic acid probe for the gene. The detection of a labeled nucleic acid at the probe position indicates that the targeted gene has been expressed.

Various methods of RNA detection have been developed. These include the "Northern" blotting procedure and the use of radioactive isotobes such as $^{32}P$. Non-radioactive detection techniques have also been developed. Langer et al., Proc. Natl. Acad. Sci. USA 1981, 78, 6633-6637, for example, disclosed certain biotin labeled nucleosides. Lockhart et al., U.S. Pat. No. 6,344,316, disclosed enzymatic methods of end-labeling a with non-radioactive nucleotides. These references are each incorporated herein for all purposes by reference.

There remains, however, a need for RNA labeling compounds which can be used for efficient and accurate labeling of RNA and monitoring of gene expression.

SUMMARY OF THE INVENTION

In one aspect of the present invention, compounds are provided which can be used for ligating detectable moieties onto the 3' end of RNA molecules or fragments thereof. In one aspect of the present invention, compounds are provided of the formula

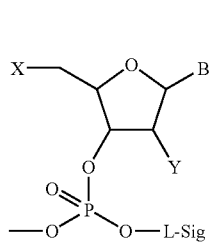

wherein B is a heterocyclic base moiety; X is a functional group which permits attachment of the nucleic acid labeling compound to the 3' OH group of the RNA molecule or RNA fragment; Y is selected from the group consisting of —H, —OH, —OR, —SR, —NHR, or a halogen; L is a linker group; and Sig is a detectable label or moiety.

In accordance with another aspect of the instant invention, a nucleic acid labeling compound according to the formula

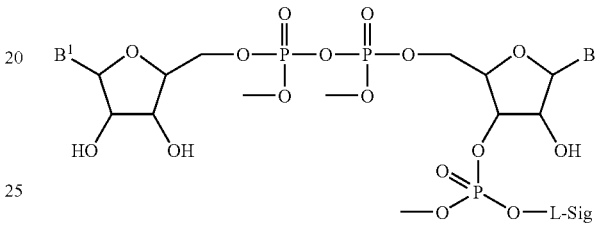

is provided, wherein L is a linker and Sig is a detectable moiety; $B_1$ is adenine and B is selected the group consisting of adenine, guanine, cytosine, and uracil.

In accordance with yet another aspect of the present invention, compounds are presented having multiple signal sources such as the following formula:

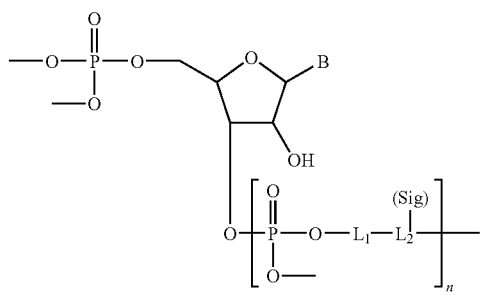

wherein B is a heterocyclic base moiety, $L_1$ is a first linker, $L_2$ is a second linker, Sig is a detectable moiety and n is an integer from 1 to 6.

In another aspect of the invention, a method is provided for end-labeling RNA (total RNA, mRNA, cRNA or fragmented RNA). In one embodiment, T4 RNA ligase is used to attach a 3'-biotinylated AMP or CMP donor to an RNA acceptor molecule. In another embodiment, a pyrophosphate of the form 3'-AppN-3'-linker-biotin is used as donor molecule to be ligated to an RNA acceptor molecule.

In another aspect of the invention, a method is provided for analyzing a nucleic acid population on a nucleic acid microarray comprising providing a nucleic acid population or converting the nucleic acid population into nucleic acid fragments; ligating the nucleic acid population or fragments to a nucleic acid labeling molecule to form labeled nucleic acid population or fragments using a ligase; hybridizing the labeled nucleic acid population or fragments to an array of nucleic acid probes, and determining hybridization signals of the probes as an indication of levels of the nucleic acids in the nucleic acid population.

DETAILED DESCRIPTION OF THE INVENTION

Figure 1:
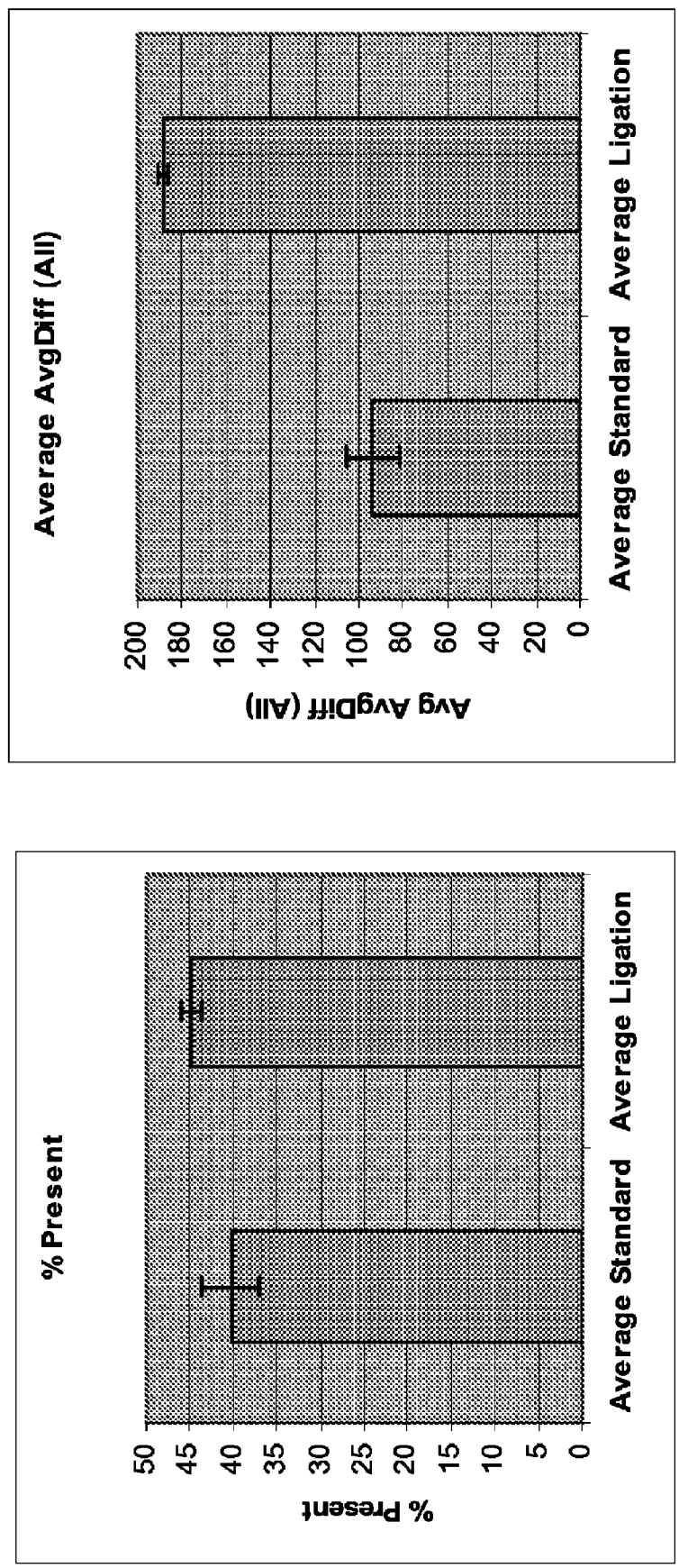
FIG. 1: Comparison of replicate end-labeled (Average Ligation) vs. internally-labeled cRNA (Average Standard) based on four replicates of each. End-labeling by ligation results in a greater number of present calls and higher target intensity (as measured by the average average difference) compared to internally-labeled cRNA.

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example hereinbelow. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, Biochemistry, (WH Freeman), Gait, "Oligonucleotide Synthesis: A Practical Approach" 1984, IRL Press, London, all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, and 6,136,269, in PCT Applications Nos. PCT/US99/00730 (International Publication Number WO 99/36760) and PCT/US01/04285, and in U.S. patent application Ser. Nos. 09/501,099 and 09/122,216 which are all incorporated herein by reference in their entirety for all purposes. Preferred arrays are commercially available from Affymetrix, Inc. (Santa Clara, Calif.). See www.affymetrix.com.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

The present invention also contemplates many uses for polymers attached to solid substrates. These uses include gene expression monitoring, profiling, library screening, genotyping, and diagnostics. Gene expression monitoring, and profiling methods can be shown in U.S. Pat. Nos. 5,800,992, 6,013,449, 6,020,135, 6,033,860, 6,040,138, 6,177,248 and 6,309,822. Genotyping and uses therefor are shown in U.S. Ser. No. 10/013,598, and U.S. Pat. Nos. 5,856,092, 6,300,063, 5,858,659, 6,284,460 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. For example, see the patents in the gene expression, profiling, genotyping and other use patents above, as well as U.S. Ser. No. 09/854,317, Wu and Wallace, Genomics 4, 560 (1989), Landegren et al., Science 241, 1077 (1988), Burg, U.S. Pat. Nos. 5,437,990, 5,215,899, 5,466,586, 4,357,421, Gubler et al., 1985, Biochemica et Biophysica Acta, Displacement Synthesis of Globin Complementary DNA: Evidence for Sequence Amplification, transcription amplification, Kwoh et al., Proc. Natl. Acad. Sci. USA 86, 1173 (1989), Guatelli et al., Proc. Nat. Acad. Sci. USA, 87, 1874 (1990), WO 88/10315, WO 90/06995, and 6,361,947.

The present invention also contemplates detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625 and in PCT Application PCT/US99/06097 (published as WO99/47964), each of which also is hereby incorporated by reference in its entirety for all purposes.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over the internet. See provisional application 60/349,546.

Definitions

An "nucleic acid array" refers to a multiplicity of different oligonucleotides or polynucleotides attached (preferably through a single terminal covalent bond) to one or more solid supports where, when there is a multiplicity of supports, each support bears a multiplicity of oligonucleotides or polynucleotides. The term "array" can refer to the entire collection of oligonucleotides or polynucleotides on the support(s) or to a subset thereof. The spatial distribution of the oligonucleotide or polynucleotide species may differ between the two arrays, but, in a preferred embodiment, it is substantially the same. It is recognized that even where two arrays are designed and synthesized to be identical there are variations in the abundance, composition, and distribution of oligonucleotide or polynucleotide probes. These variations are preferably insubstantial and/or compensated for by the use of controls as described herein. The terms oligonucleotide and polynucleotide can be used interchangeably in this application and the use of one term should not appear as a limitation of the invention.

The terms "nucleic acid" or "nucleic acid molecule" refer to a deoxyribonucleotide or ribonucleotide polymer in either single- or double-stranded form, and unless otherwise limited, would encompass known analogs of natural nucleotides that can function in a similar manner as naturally occurring nucleotides.

An oligonucleotide or polynucleotide is a single-stranded nucleic acid ranging in length from 2 to about 1000 nucleotides, more typically from 2 to about 500 nucleotides in length.

As used herein a "probe" is defined as an oligonucleotide or polynucleotide capable of binding to a target nucleic acid of complementary sequence through one or more types of chemical bonds, usually through complementary base pairing, usually through hydrogen bond formation. As used herein, an oligonucleotide or polynucleotide probe may include natural (i.e. A, G, C, or T) or modified bases (7-deazaguanosine, inosine, etc.). In addition, the bases in oligonucleotide or polynucleotide probe may be joined by a linkage other than a phosphodiester bond, so long as it does not interfere with hybridization. Thus, oligonucleotide or polynucleotide probes may be peptide nucleic acids in which the constituent bases are joined by peptide bonds rather than phosphodiester linkages. Oligonucleotide or polynucleotide probes may also be generically referred to as nucleic acid probes.

The term "target nucleic acid" refers to a nucleic acid (often derived from a biological sample and hence referred to also as a sample nucleic acid), to which the oligonucleotide or polynucleotide probe specifically hybridizes. It is recognized that the target nucleic acids can be derived from essentially any source of nucleic acids (e.g., including, but not limited to chemical syntheses, amplification reactions, forensic samples, etc.) It is either the presence or absence of one or more target nucleic acids that is to be detected, or the amount of one or more target nucleic acids that is to be quantified. The target nucleic acid(s) that are detected preferentially have nucleotide sequences that are complementary to the nucleic acid sequences of the corresponding probe(s) to which they specifically bind (hybridize). The term target nucleic acid may refer to the specific subsequence of a larger nucleic acid to which the probe specifically hybridizes, or to the overall sequence (e.g., gene or mRNA) whose abundance (concentration) and/or expression level it is desired to detect. The difference in usage will be apparent from context.

The phrase "coupled to a support" means bound directly or indirectly thereto including attachment by covalent binding, hydrogen bonding, ionic interaction, hydrophobic interaction, or otherwise.

A "detectable moiety" or "labeled moiety" means a molecule or complex of molecules and or particles capable of being detected by various equipment and or tests (comprising physical, chemical, electrical and/or computer based) methods of detecting the moiety when attached for example to a nucleic acid.

"Bind(s) substantially" refers to complementary hybridization between a probe nucleic acid and a target nucleic acid and embraces minor mismatches that can be accommodated by reducing the stringency of the hybridization media to achieve the desired detection of the target oligonucleotide or polynucleotide sequence.

The phrase "hybridizing specifically to", refers to the binding, duplexing, or hybridizing of a molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is at least about 0.01 to 1.0 M Na ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide.

The terms "background" or "background signal intensity" refer to hybridization signals resulting from non-specific binding, or other interactions, between the labeled target nucleic acids and components of the oligonucleotide or polynucleotide array (e.g., the oligonucleotide or polynucleotide probes, control probes, the array substrate, etc.). Background signals may also be produced by intrinsic fluorescence of the array components themselves. A single background signal can be calculated for the entire array, or a different background signal may be calculated for each region of the array. In a preferred embodiment, background is calculated as the average hybridization signal intensity for the lowest 1% to 10% of the probes in the array, or region of the array. In expression monitoring arrays (i.e., where probes are preselected to hybridize to specific nucleic acids (genes)), a different background signal may be calculated for each target nucleic acid. Where a different background signal is calculated for each target gene, the background signal is calculated for the lowest 1% to 10% of the probes for each gene. Of course, one of skill in the art will appreciate that where the probes to a particular gene hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g. probes directed to nucleic acids of the opposite sense or to genes not found in the sample such as bacterial genes where the sample is of mammalian origin). Background can also be calculated as the average signal intensity produced by regions of the array that lack any probes at all.

The term "quantifying" when used in the context of quantifying nucleic acid abundances or concentrations (e.g., transcription levels of a gene) can refer to absolute or to relative quantification. Absolute quantification may be accomplished by inclusion of known concentration(s) of one or more target nucleic acids (e.g. control nucleic acids such as BioB or with known amounts the target nucleic acids themselves) and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

Nucleic Acid Labeling

In one aspect of the present invention, the hybridized nucleic acids are detected by detecting one or more labels attached to the sample nucleic acids. The labels may be incorporated by any of a number of means well known to those of skill in the art. However, in a preferred embodiment, the label is simultaneously incorporated during the amplification step in the preparation of the sample nucleic acids. For example, polymerase chain reaction (PCR) with labeled primers or labeled nucleotides will provide a labeled amplification product. The nucleic acid (e.g., DNA) is be amplified in the presence of labeled deoxynucleotide triphosphates (dNTPs). The amplified nucleic acid can be fragmented, exposed to an oligonucleotide array, and the extent of hybridization determined by the amount of label now associated with the array. In a preferred embodiment, transcription amplification, as described above, using a labeled nucleotide (e.g. fluorescein-labeled UTP and/or CTP) incorporates a label or moiety into the transcribed nucleic acids.

Alternatively, a label may be added directly to the original nucleic acid sample (e.g., mRNA, polyA mRNA, cDNA, etc.) or to the amplification product after the amplification is completed. Such labeling can result in the increased yield of amplification products and reduce the time required for the amplification reaction. Means of attaching labels to nucleic acids include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

In many applications it is useful to directly label nucleic acid samples without having to go through amplification, transcription or other nucleic acid conversion step. This is especially true for monitoring of mRNA levels where one would like to extract total cytoplasmic RNA or poly A+ RNA (mRNA) from cells and hybridize this material without any intermediate steps. See U.S. Pat. No. 6,344,316, which is hereby incorporated by reference in its entirety for all purposes.

End labeling can be performed using terminal transferase (TdT). End labeling can also be accomplished by ligating a labeled nucleotide or oligonucleotide or polynucleotide or analog thereof to the end of a target nucleic acid or probe. See U.S. Pat. No. 6,344,316.

According to one aspect of the present invention, methods of end labeling a nucleic acid and reagents useful therefore are described. In one preferred embodiment of the present invention, the method involves providing a nucleic acid, providing a labeled nucleotide or oligonucleotide or polynucleotide and enzymatically ligating the nucleotide or oligonucleotide or polynucleotide to the nucleic acid. Thus, according to one aspect of the present invention, where the nucleic acid is an RNA, a labeled ribonucleotide can be ligated to the RNA using an RNA ligase. RNA ligase catalyzes the covalent joining of single-stranded RNA (or DNA, but the reaction with RNA is more efficient) with a 5' phosphate group to the 3'-OH end of another piece of RNA (or DNA). The specific requirements for the use of this enzyme are described in The Enzymes, Volume XV, Part B, T4 RNA Ligase, Uhlenbeck and Greensport, pages 31-58; and 5.66-5.69 in Sambrook et al., Molecular Cloning, A Laboratory Manual, Cold Spring Harbor Press, Cold Spring Harbor, N.Y. (1982), all of which are incorporated here by reference in full.

According to one aspect of the present invention, a method is provided for adding a label to a nucleic acid (e.g. extracted RNA) directly rather than incorporating labeled nucleotides in a nucleic acid polymerization step. According to one aspect of the present invention this may be accomplished by adding a labeled ribonucleotide or short labeled oligoribonucleotide to the ends of a single stranded nucleic acid.

In accordance with one aspect of the present invention, an RNA labeling compound can be directly ligated to the '3-OH group of an RNA molecule without any processing of the molecule. For example microRNAs (miRNAs) are an extensive class of small noncoding RNAs (approximately 15-25 nucleotides). It is believed that these RNAs play a role in the regulation of Gene Expression. For example in *Caenorhabditis elegans*, lin-4 and let-7 miRNAs control the timing of fate specification of neuronal and hypodermal cells during larval development. Lagos-Quintana M, Rauhut R, Lendeckel W, Tuschl T: Identification of novel genes coding for small expressed RNAs. *Science* 2001, 294:853-858. The enzymatic machinery involved in the biogenesis of miRNAs in plants and animals has been extensively studied. RNAse type III-like Dicer, together with Argonaute proteins, cleaves a miRNA hairpin precursor (70 to 75 nucleotides) to yield a stable, ~22 nucleotides miRNA from one arm of the hairpin. Ke X S, Liu C M, Liu D P, Liang CC: MicroRNAs: key participants in gene regulatory networks. *Curr Opin Chem Biol* 2003, 7:516-523.

It is understood by those of skill in the art that miRNAs have free 3' OH groups. Hence, the nucleic acid labeling molecules of the instant invention can be directly ligated onto the end of such RNAs without pre-fragmentation or de-phosphorylation as is required for mRNA or cRNA.

RNA can be randomly fragmented with heat in the presence of $Mg^{2+}$. This generally produces RNA fragments with 5' OH groups and phosphorylated 3' ends. According to one aspect of the present invention, alkaline phosphatase is used to remove the phosphate group from the 3' ends of the RNA fragment. In accordance with one aspect of the present invention, a donor comprising a ribonucleotide having a detectable moiety and having a 5'-terminal phosphate is then ligated to the 3' OH group of the RNA fragments using T4 RNA ligase to provide a labeled RNA. The donor is also called, in accordance with the present invention, a nucleic acid labeling compound.

T4 RNA ligase catalyzes ligation of a 5' phosphoryl-terminated nucleic acid donor to a 3' hydroxyl-terminated nucleic acid acceptor through the formation of a 3' to 5' phosphodiester bond, with hydrolysis of ATP to AMP and PPi. Although the minimal acceptor must be a trinucleoside diphosphate, dinucleoside pyrophosphates (NppN) and mononucleoside 3',5'-disphosphates (pNp) are effective donors in the intermolecular reaction. See Hoffmann and McLaughlin, *Nuc. Acid. Res.* 15, 5289-5303 (1987), which is hereby incorporated by reference in its entirety for all purposes.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oreg., USA), radiolabels (e.g., 3H, 125I, 35S, 14C, or 32P), enzymes (e.g., horse radish peroxidase, alkaline phosphatase and others commonly used in an ELISA), and calorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is preferred because it provides a very strong signal with low background. It is also optically detectable at high resolution and sensitivity through a quick scanning procedure. The nucleic acid samples can all be labeled with a single label, for example, a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish cites of binding of the red label from those binding the green fluorescent label. Each nucleic acid sample (target nucleic acid) can be analyzed independently from one another.

Hybridization

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label or moiety. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6×SSPE-T at about 40° C. to about 50° C. (0.005% Triton X-100) to ensure hybridization and then subsequent washes are performed at higher stringency (e.g., 1×SSPE-T at 37° C.) to eliminate mismatched hybrid duplexes. Successive washes may be performed at increasingly higher stringency (e.g., down to as low as 0.25× SSPE-T at 37° C. to 50° C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide or polynucleotide probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.1 to about 0.5 mg/ml DNA (e.g., herring sperm DNA). The use of blocking agents in hybridization is well known to those of skill in the art (see, e.g., Chapter 8 in P. Tijssen, supra.)

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altered duplex stability conferred by using oligonucleotide or polynucleotide analogue probes can be ascertained by following, e.g., fluorescence signal intensity of oligonucleotide or polynucleotide analogue arrays hybridized with a target oligonucleotide or polynucleotide over time. The data allow optimization of specific hybridization conditions at, e.g., room temperature (for simplified diagnostic applications in the future).

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature. Methods of optimizing hybridization conditions are well known to those of skill in the art (see, e.g., *Laboratory Techniques in Biochemistry and Molecular Biology, Vol. 24: Hybridization With Nucleic Acid Probes*, P. Tijssen, ed. Elsevier, N.Y., (1993)).

Labeled Nucleotides

According to one aspect of the present invention, T4 RNA ligase is used to enzymatically incorporate a nucleic acid labeling compound into an RNA or fragmented RNA population. T4 RNA ligase catalyzes ligation of a 5' phosphoryl-terminated nucleic acid donor to a 3' hydroxyl-terminated nucleic acid acceptor through the formation of a 3' to 5' phosphodiester bond, with hydrolysis of ATP to AMP and PPi. Although the minimal acceptor must be a trinucleoside diphosphate, dinucleoside pyrophosphates (NppN) and mononucleoside 3',5'-disphosphates (pNp) are effective donors in the intermolecular reaction. See, for example, Richardson, R. W. and Gumport, R. I. (1983), *Nuc. Acid Res:* 11, 6167-6185 and England, T. E., Bruce, A. G., and Uhlenbeck, O. C. (1980), *Meth. Enzymol* 65, 65-74, which are hereby incorporated by reference in its entirety for all purposes.

According to one aspect of the present invention, a method is disclosed for end-labeling fragmented RNA (total RNA, mRNA or cRNA) prior to hybridization to a DNA microarray. The system uses T4 RNA ligase to attach a 3'-biotinylated AMP (or CMP) donor to the 3'-end of an RNA acceptor molecule. T4 RNA ligase catalyses the formation of an internucleotide phosphodiester bond between an oligonucleotide or polynucleotide donor molecule with a 5'-terminal phosphate and an oligonucleotide or polynucleotide acceptor molecule with a 3'-terminal hydroxyl. Although the minimal acceptor must be a trinucleoside diphosphate, dinucleoside pyrophosphates (NppN) and mononucleoside 3',5'-disphosphates (pNp) are effective donors in the intermolecular reaction.

This technique can be used to label an RNA target and uses commonly available labeling moieties and enzymes. cRNA can be produced using current GeneChip® Array (Affymetrix, Inc., Santa Clara, Calif.) expression protocols (except in vitro transcription is performed with standard nucleotides) followed by dephosphorylation and ligation to an appropriate nucleic acid labeling compound as disclosed with respect to the present invention.

Detectable Molecules

A detectable moiety provides the signal either directly or indirectly. A direct signal is produced where the labeling group spontaneously emits a signal, or generates a signal upon the introduction of a suitable stimulus. Radiolabels, such as $^3$H, $^{125}$I, $^{35}$S, $^{14}$C or $^{32}$P, and magnetic particles, such as Dynabeads™, are nonlimiting examples of groups that directly and spontaneously provide a signal. Labeling groups that directly provide a signal in the presence of a stimulus include the following nonlimiting examples: colloidal gold (40-80 nm diameter), which scatters green light with high efficiency; fluorescent labels, such as fluorescein, texas red, rhodamine, and green fluorescent protein (Molecular Probes, Eugene, Oreg.), which absorb and subsequently emit light; chemiluminescent or bioluminescent labels, such as luminol, lophine, acridine salts and luciferins, which are electronically excited as the result of a chemical or biological reaction and subsequently emit light; spin labels, such as vanadium, copper, iron, manganese and nitroxide free radicals, which are detected by electron spin resonance (ESR) spectroscopy; dyes, such as quinoline dyes, triarylmethane dyes and acridine dyes, which absorb specific wavelengths of light; and colored glass or plastic (e.g., polystyrene, polypropylene, latex, etc.) beads. See U.S. Pat. Nos. 3,817,837; 3,850,752; 3,939,350; 3,996,345; 4,277,437; 4,275,149 and 4,366,241.

A detectable moiety provides an indirect signal where it interacts with a second compound that spontaneously emits a signal, or generates a signal upon the introduction of a suitable stimulus.

Biotin is particularly preferred detectable moiety. Biotin produces a signal by forming a conjugate with streptavidin, which is then detected. See Hybridization With Nucleic Acid Probes. In *Laboratory Techniques in Biochemistry and Molecular Biology*; Tijssen, P., Ed.; Elsevier: New York, 1993; Vol. 24. An enzyme, such as horseradish peroxidase or alkaline phosphatase, that is attached to an antibody in a label-antibody-antibody as in an ELISA assay, also produces an indirect signal. In preferred embodiments, multiple Sig groups are incorporated into the nucleic acid labeling compound. In particularly preferred embodiments of the present invention, multiple biotin groups which may act to boost or enhance the ability of the Sig group to be detected.

A preferred detectable moiety is a fluorescent group. Flourescent groups typically produce a high signal to noise ratio, thereby providing increased resolution and sensitivity in a detection procedure. Preferably, the fluorescent group absorbs light with a wavelength above about 300 nm, more preferably above about 350 nm, and most preferably above about 400 nm. The wavelength of the light emitted by the fluorescent group is preferably above about 310 nm, more preferably above about 360 nm, and most preferably above about 410 nm.

The fluorescent detectable moiety is selected from a variety of structural classes, including the following nonlimiting examples: 1- and 2-aminonaphthalene, p,p'diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolyl phenylamine, 2-oxo-3-chromen, indole, xanthen, 7-hydroxycoumarin, phenoxazine, salicylate, strophanthidin, porphyrins, triarylmethanes, flavin, xanthene dyes (e.g., fluorescein and rhodamine dyes); cyanine dyes; 4,4-difluoro-4-bora-3a,4a-diaza-s-indacene dyes and fluorescent proteins (e.g., green fluorescent protein, phycobiliprotein).

A number of fluorescent compounds are suitable for incorporation into the present invention. Nonlimiting examples of such compounds include the following: dansyl chloride; fluoresceins, such as 3,6-dihydroxy-9-phenylxanthhydrol; rhodamineisothiocyanate; N-phenyl-1-amino-8-sulfonatonaphthalene; N-phenyl-2-amino-6-sulfonatonaphthanlene; 4-acetamido-4-isothiocyanatostilbene-2,2'-disulfonic acid; pyrene-3-sulfonic acid; 2-toluidinonapthhalene-6-sulfonate; N-phenyl, N-methyl 2-aminonaphthalene-6-sulfonate; ethidium bromide; stebrine; auromine-0,2-(9'-anthroyl)palmitate; dansyl phosphatidylethanolamine; N,N'-dioctadecyl oxacarbocycanine; N,N'-dihexyl oxacarbocyanine; merocyanine, 4-(3'-pyrenyl)butyrate; d-3-aminodesoxy-equilenin; 12-(9'-anthroyl)stearate; 2-methylanthracene; 9-vinylanthracene; 2,2'-(vinylene-p-phenylene) bisbenzoxazole; p-bis[2-(4-methyl-5-phenyl oxazolyl)] benzene; 6-dimethylamino-1,2-benzophenzin; retinol; bis (3'-aminopyridinium)-1,10-decanediyl diiodide; sulfonaphthylhydrazone of hellibrienin; chlortetracycline; N-(7-dimethylamino-4-methyl-2-oxo-3-chromenyl)maleimide; N-[p-(2-benzimidazolyl)phenyl]maleimide; N-(4-fluoranthyl)maleimide; bis(homovanillic acid); resazarin; 4-chloro-7-nitro-2,1,3-benzooxadizole; merocyanine 540; resorufin; rose bengal and 2,4-diphenyl-3(2H)-furanone. Preferably, the fluorescent detectable moiety is a fluorescein or rhodamine dye.

Another preferred detectable moiety is colloidal gold. The colloidal gold particle is typically 40 to 80 nm in diameter. The colloidal gold may be attached to a labeling compound in a variety of ways. In one embodiment, the linker moiety of the nucleic acid labeling compound terminates in a thiol group (—SH), and the thiol group is directly bound to colloidal gold through a dative bond. See Mirkin et al. *Nature* 1996, 382, 607-609. In another embodiment, it is attached indirectly, for instance through the interaction between colloidal gold conjugates of antibiotin and a biotinylated labeling compound. The detection of the gold labeled compound may be enhanced through the use of a silver enhancement method. See Danscher et al. *J. Histotech* 1993, 16, 201-207.

In accordance with the present invention, a method is presented of detecting the presence of an RNA of interest, the method having the following steps: providing a sample of RNA which may or may not have said RNA of interest; ligating the RNA to a labeling reagent having the formula

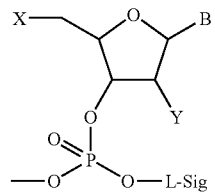

wherein B is a heterocyclic base moiety; X is a functional group which permits attachment of the nucleic acid labeling compound to the 3' OH group of said fragments; Y is selected from the group consisting of —H, —OH, —OR, —SR, —NHR, or a halogen; L is a linker group; and Sig is a detectable moiety to provide labeled RNAs; providing a nucleic acid array having probes directed to said RNA of interest; hybridizing the labeled RNAs to said nucleic acid array; and determining the extent of hybridization to said probes to determine the presence of said RNA of interest.

In accordance with the above aspect of the present invention, RNA comprises microRNA. For longer RNAs such as cRNAs or mRNAs the method may further have the steps of treating the sample with a fragmenting reagent to provide RNA fragments; and removing phosphate groups from said fragments to provide fragments with free 3' OH groups after said step of providing said sample and before said step of ligating. 3' phosphate groups are a common product of fragmenting reagents such as Mg or RNAseIII. The phosphate group must be removed to allow the ligase to add the nucleic acid labeling compound. Hence, for this aspect of the instant invention mRNA and cRNA are preferred. However, it is understood the microRNAS do not have 3' phosphate groups and they are by nature short, less than 25 nucleotides. Thus, they do not require fragmentation or phosphatase treatment.

Preferred fragmenting reagent are selected from the group consisting of RNAse III and a buffer containing a divalent metal ion such as $Mg^{2+}$ and having a pH in the neutral to alkaline range. Phosphate groups may be removed from 3' hydroxyl groups with alkaline phosphatase.

X is preferably selected from the group consisting of HO—, $PO_4^{2-}$—, $P_2O_7^{3-}$—, $P_3O_{10}^{4-}$—, $OP(S)O_2^{2-}$ and adenosine-(5')—$P_2O_7^-$—, having appropriate counter ions selected from the group consisting of as $H^+$, $Li^+$, $Na^+$, $NH4^+$ or $K^+$. Y is preferably OH. Lisase is preferably T4 RNA ligase. It is preferred that the nucleic acid arrays are oligonucleotide arrays. More preferably, oligonucleotide array are prepared by photolithography.

The linker group is preferably selected from the group consisting of —$CH_2$—CH(OH)—$CH_2$—(O—$CH_2$—$CH_2$)$_3$—O—$CH_2$—$CH_2$—$CH_2$—NH— and —$CH_2$—CH(OPO$_3^-$)—$CH_2$—(O—$CH_2$—$CH_2$)$_3$—O—$CH_2$—$CH_2$—$CH_2$—NH—. More preferably, L is —$CH_2$—CH(OH)—$CH_2$—(O—$CH_2$—$CH_2$)$_3$—O—$CH_2$—$CH_2$—$CH_2$—NH—.

According to one aspect of the present invention, X is $PO_4^{2-}$. B is selected from the group consisting of a pyrimidine base, a purine base, a natural base analog and an unnatural analogue. More preferably, B is selected from the group of consisting of adenine, guanine, cytosine, and uracil. More preferably, B is selected from the group of adenine and cytosine. Most preferably, B is cytosine.

A preferred labeling reagent is

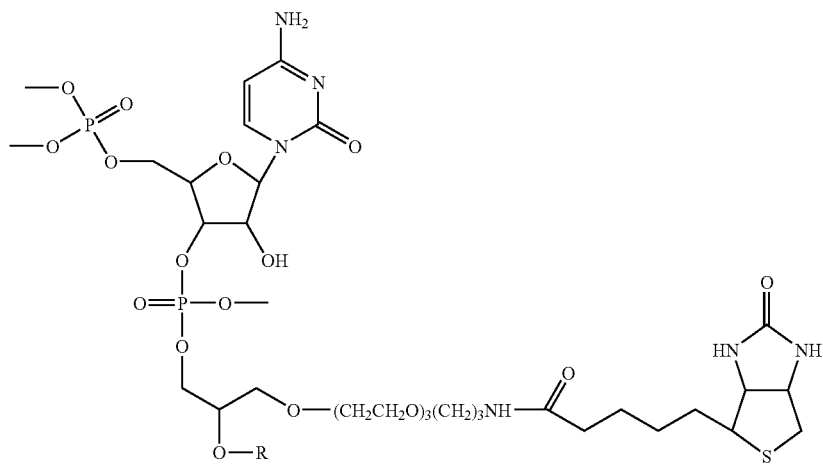

wherein R is H or $PO_3^{2-}$. Preferably R is H. Another preferred labeling reagent is

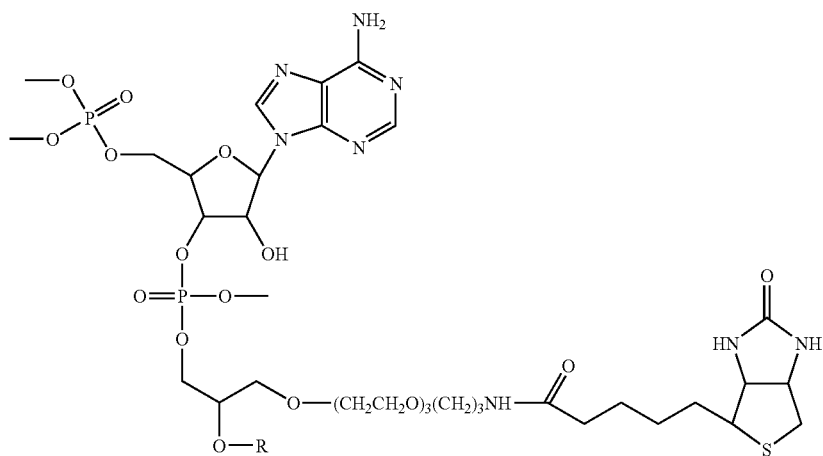

wherein R is H or $PO_3^{2-}$. Preferably R is H.

Another preferred labeling reagent is the following structure

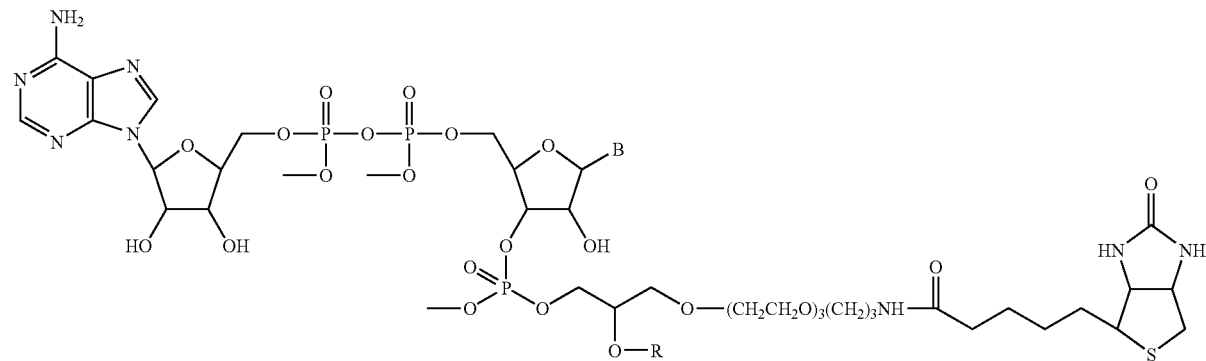

wherein B is selected from the group consisting of adenine, guanine, cytosine, and uracil; and R is H or $PO_3^=$. Preferably, B is selected from the group of adenine and cytosine and R is H. More preferably B is adenine. In another preferred embodiment, B is cytosine and R is H.

A preferred method of detecting the presence of an RNA of interest, has the following steps; providing a sample comprising RNA which may or may not have said RNA of interest; ligating said RNA with a labeling reagent having the formula

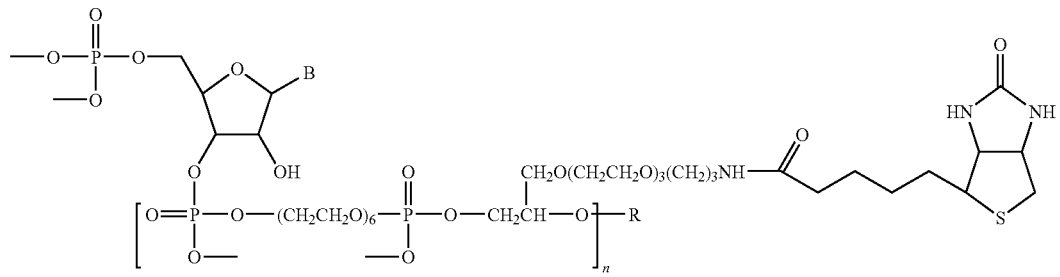

where B is a heterocyclic moiety; and R is selected from the group consisting of H and $PO_3^=$ and n is 1 to 6; providing a nucleic acid array with probes corresponding to said gene of interest; hybridizing the labeled nucleic acid fragments to a nucleic acid array; and determining the extent of hybridization to said probes to determine the presence of said RNA of interest. With respect to the above method, microRNAs are preferred.

In a preferred embodiment, the method further comprises the steps of treating the sample with a fragmenting reagent to provide RNA fragments; and removing phosphate groups from said fragments to provide fragments with free 3' OH groups after said step of providing said sample and before said step of ligating. For this procedure, mRNAs and cRNAs are preferred as templates.

Preferably, the fragmenting agent is selected from the group consisting of RNAse III and A buffer containing a divalent metal ion such as Mg2+ and having a pH in the neutral to alkaline range. Removing phosphate groups from 3' hydroxyl groups is preferably carried out with alkaline phosphatase.

B is preferably selected from the group consisting of adenine, guanine, cytosine, and uracil and n is 2 to 4. More preferably, B is selected from the group of adenine and cytosine. Most preferably B is cytosine. n is preferably 2-4. More preferably, n is 3.

Preferred labeling reagents are as follows:

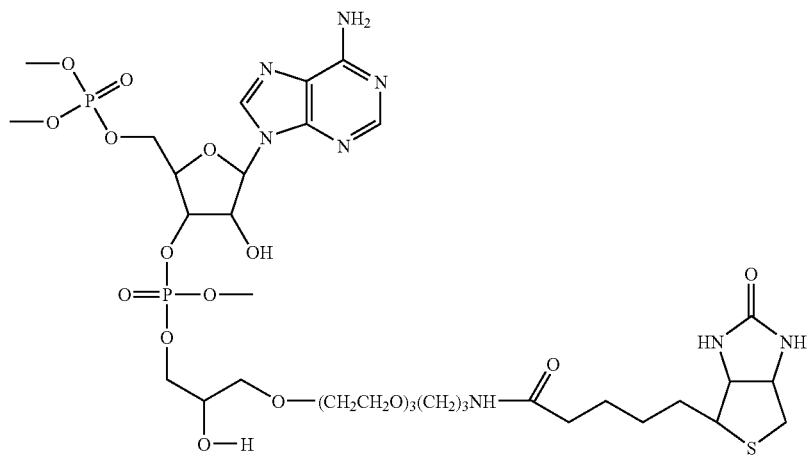

-continued
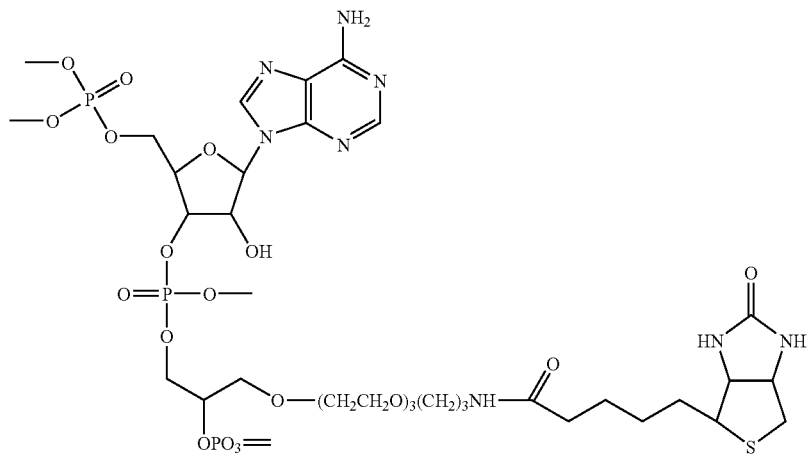
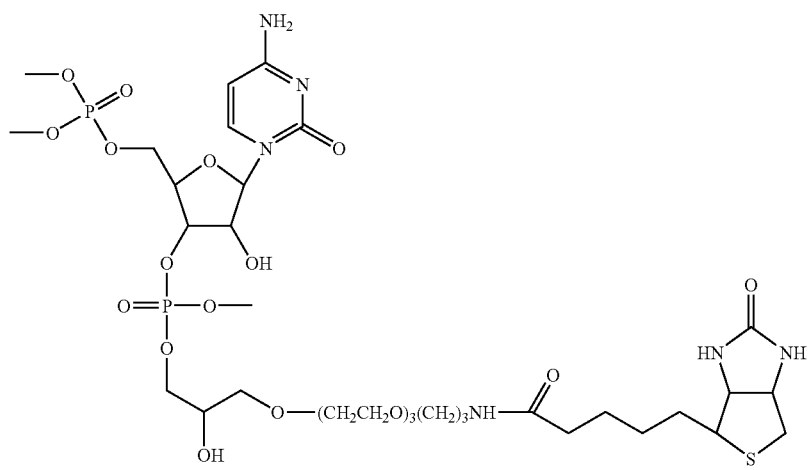
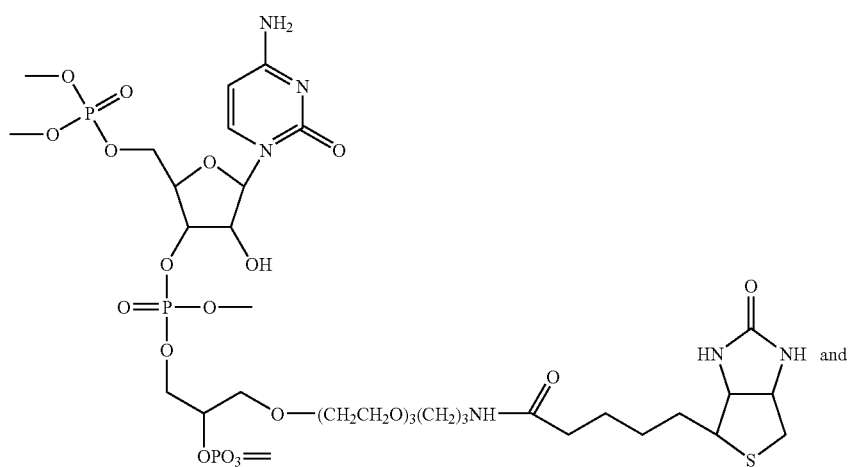

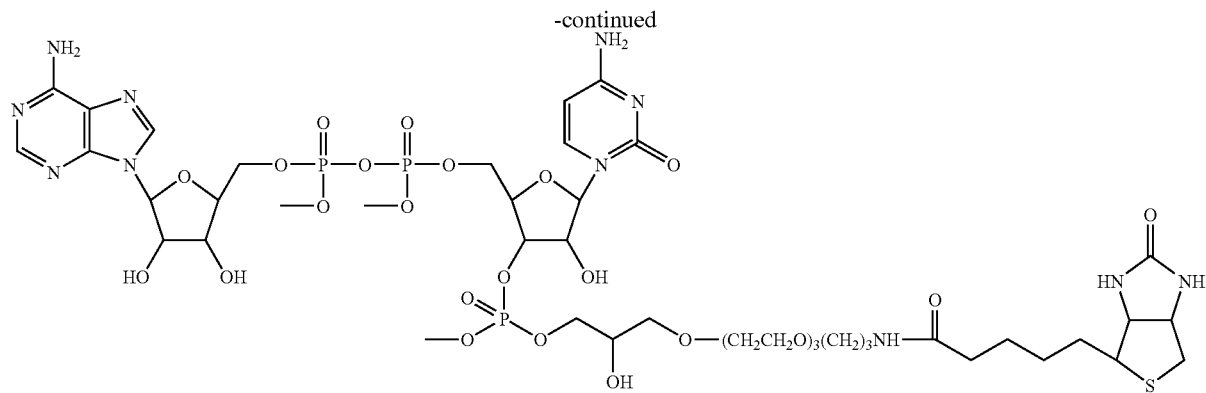
Other preferred labeling reagent is as follows:
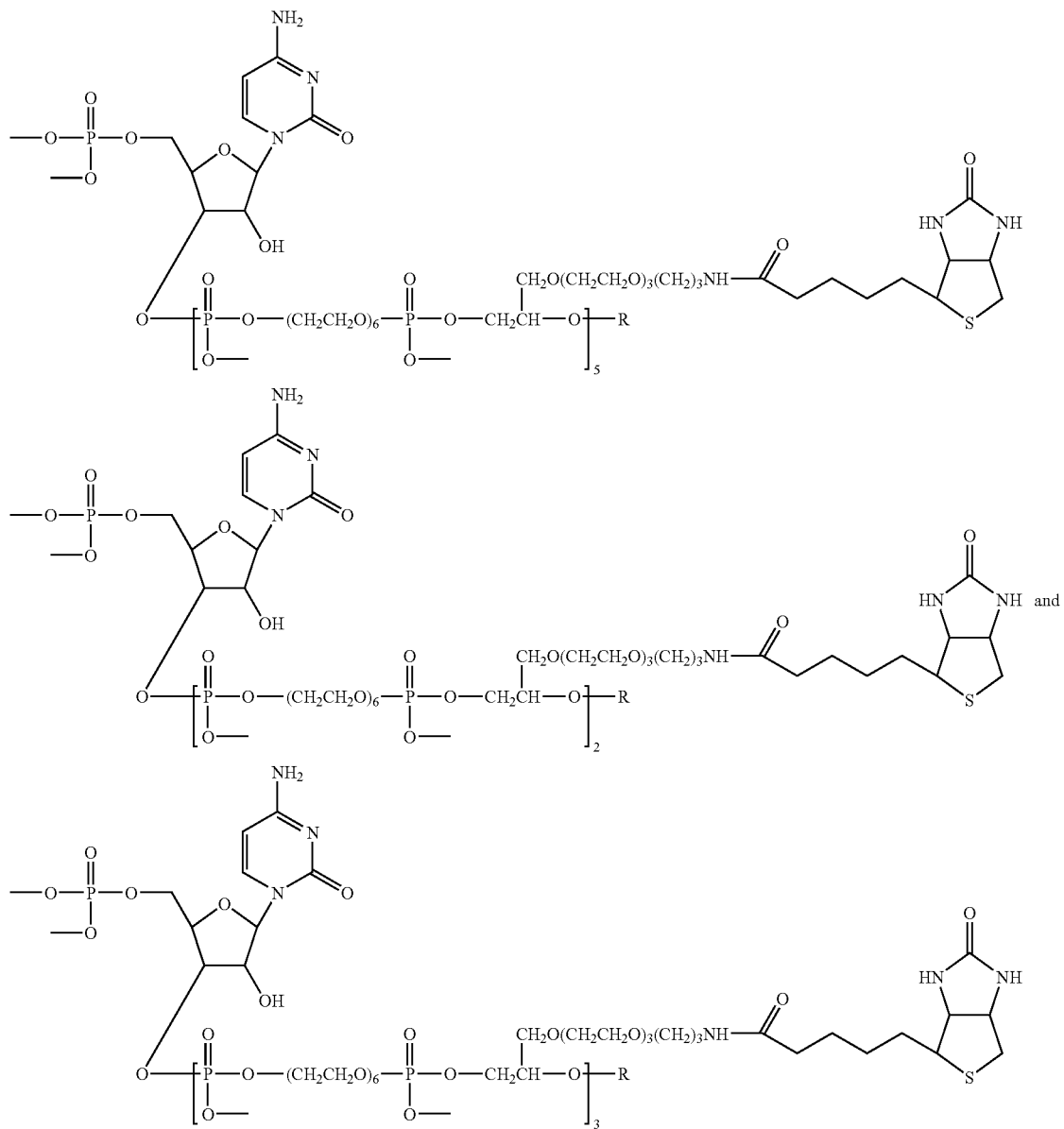

The instant invention also provides nucleic acid labeling compounds. One preferred compound is as below:

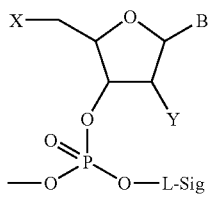

wherein B is a heterocylic base moiety; X is a functional group which permits attachment of the nucleic acid labeling compound to the 3' OH group of said fragment; Y is selected from the group consisting of —H, —OH, —OR, —SR, —NHR, or a halogen; L is a linker group; and Sig is a detectable moiety.

L is preferably selected from the group consisting of —CH$_2$—CH(OH)—CH$_2$—(O—CH$_2$—CH$_2$)$_3$—O—CH$_2$—CH$_2$—CH$_2$—NH— and —CH$_2$—CH(OPO$_3$$^=$)—CH$_2$—(O—CH$_2$—CH$_2$)$_3$—O—CH$_2$—CH$_2$—CH$_2$—NH—.

More preferably L is CH$_2$—CH(OH)—CH$_2$—(O—CH$_2$—CH$_2$)$_3$—O—CH$_2$—CH$_2$—CH$_2$—NH—.

X is preferably selected from the group consisting of HO—, PO$_4$$^{2-}$—, P$_2$O$_7$$^{3-}$—, P$_3$O$_{10}$$^{4-}$—, OP(S)O$_2$$^{2-}$ and adenosine-(5')—P$_2$O$_7$$^=$— having appropriate counter ions selected from the group consisting of as H$^+$, Li$^+$, Na$^+$, NH4$^+$ or K$^+$. Y is preferably OH. B is selected from the group consisting of a pyrimidine base, a purine base, a natural base analog and an unnatural analogue. More preferably B is selected from the group of the adenine, guanine, cytosine, and uracil. More preferably B is selected from the group of adenine and cytosine. Still more preferably, B is cytosine.

In a preferred nucleic acid labeling compound of the instant invention, the compound has the structure:

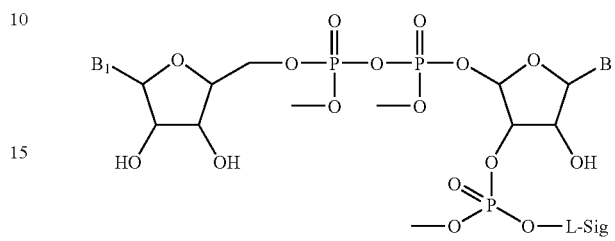

L is a linker and Sig is a detectable moiety; B$_1$ is adenine, and B is selected from the group consisting of adenine, guanine, cytosine, and uracil.

50. A nucleic acid labeling compound according to claim 44 having the formula:

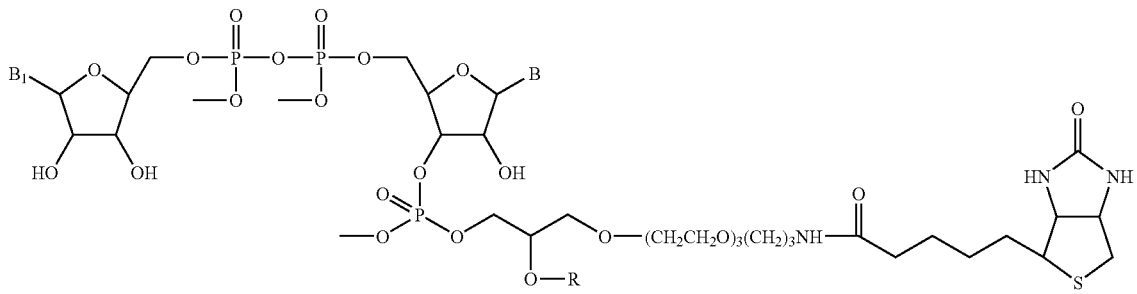

wherein B$_1$ is adenine, and B is selected from the group consisting of adenine, guanine, cytosine, and uracil; R is H or PO$_3$$^=$.

A preferred compound according to the formula above has the structure:

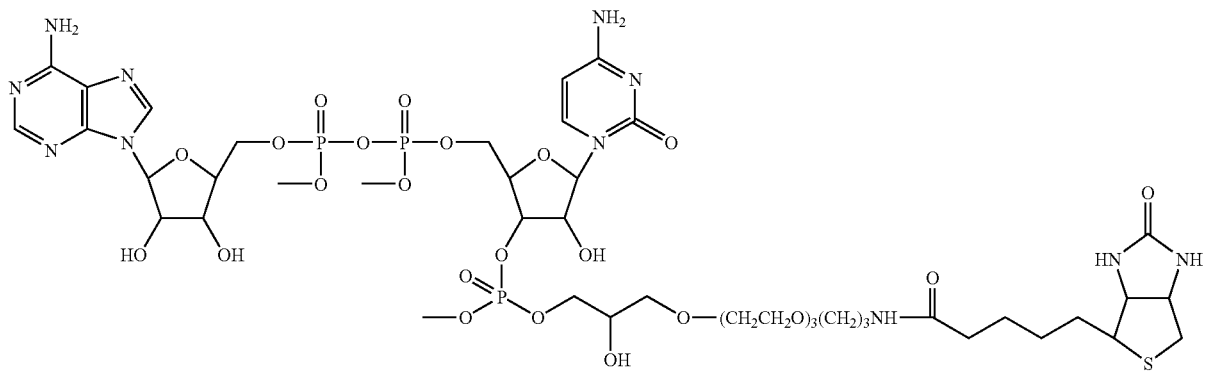

Yet another preferred compound according to the instant invention has the formula:

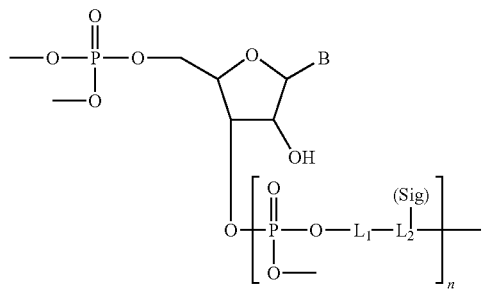

wherein B is a heterocyclic base moiety, L1 is a first linker, L2 is a second linker, Sig is a detectable moiety and n is an integer from 1 to 6.

Preferred compounds according to this aspect of the instant invention have the structure:

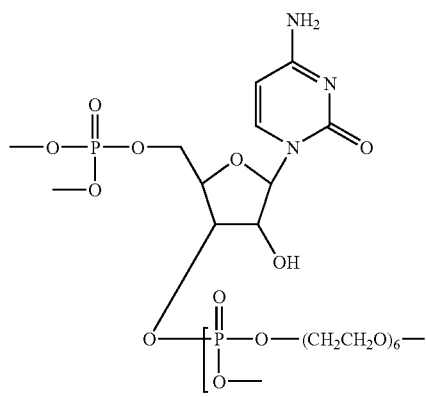

where B is a heterocyclic base moiety; and R is selected from the group consisting of H and $PO_3^=$.

The invention will be further understood by the following non-limiting examples.

EXAMPLE 1

Procedure for the Synthesis of 5'-pCp-3'-linker-biotin and 5'-pAp-3'-linker-biotin This compound was made using commercially available reagents by the solid phase phosphoramidite chemistry approach. See, e.g., U.S. Pat. No. 4,415,732; McBride, L. and Caruthers, M. *Tetrahedron Letters,* 24:245-248 (1983); and Sinha, N. et al. *Nuc. Acids Res.* 12:4539-4557 (1984), both of which are hereby incorporated by reference. The 3'-biotinylated linker derives from commercially available BiotinTEG solid support (Glenn Research, Sterling, Va.). The structure of the reagents is shown below:

biotin-TEG synthesis support

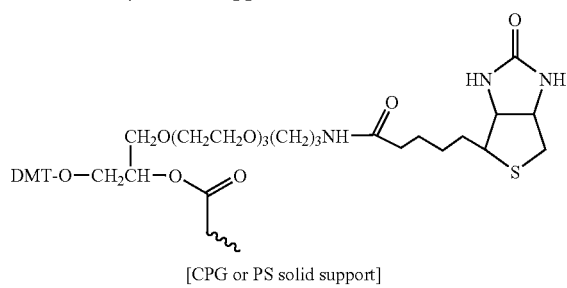

[CPG or PS solid support]

hexaethyleneglycol (HEG) phosphoramidite

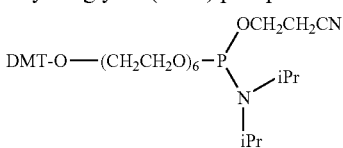

biotin-TEG phosphoramidite

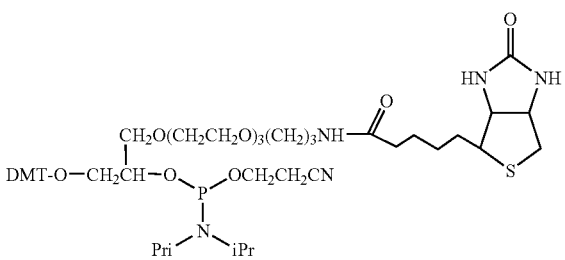

5'-phosphate-ON phosphoramidite

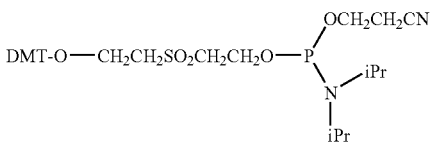

EXAMPLE 2

Procedure for the Synthesis of 3'-AppC-3'-linker-biotin Donor Molecules

The pre-adenylated pyrophosphate donor, A(5')pp(5')Cp (biotin-TEG)-3', was prepared by solution-phase condensation (FIG. 2) of p(5')Cp(biotin-TEG)-3' and adenosine-5'-monophosphoromorpholidate (Sigma), according to literature procedures (7). The product was purified by reverse-phase followed by ion-exchange HPLC to >95% purity, and characterized by MALDI-TOF MS.

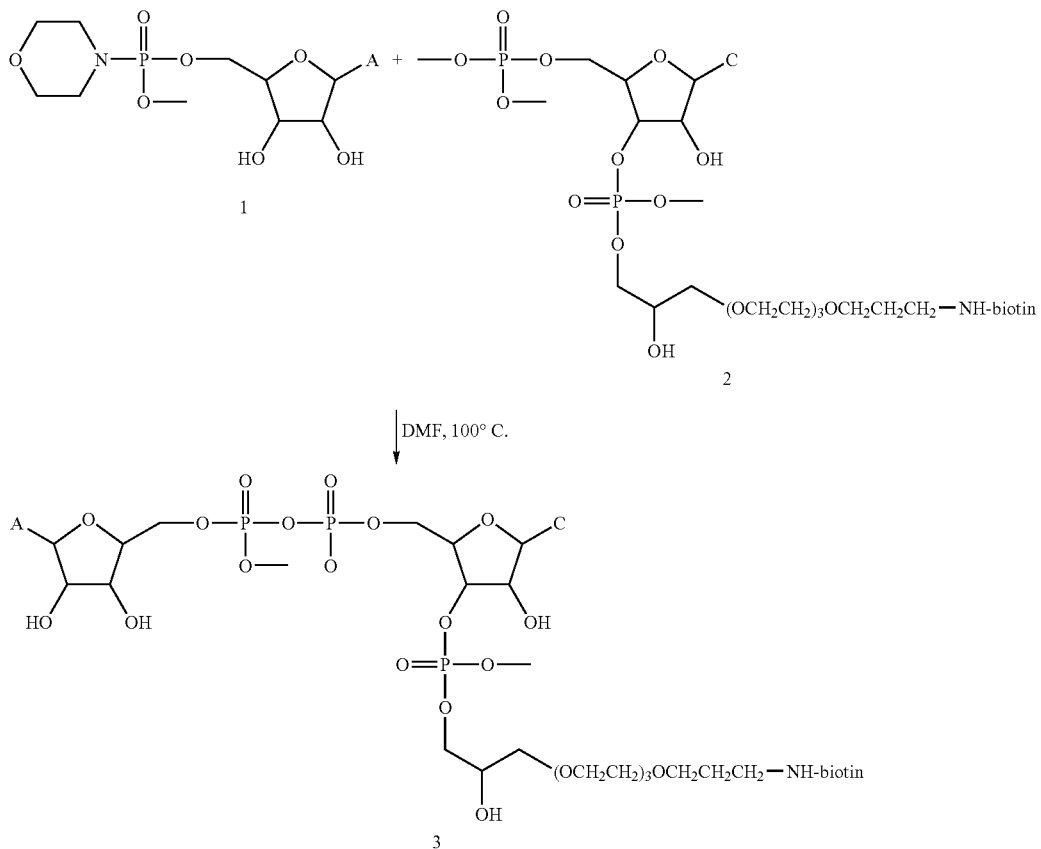

EXAMPLE 3

Controls and Preparation of Sample

Unlabeled cRNA was prepared from total RNA (1 ug of human heart RNA as starting material in these data) according to the recommended GeneChip expression protocols (Affymetrix, Inc., Santa Clara, Calif.), except that unlabeled ribonucleotides were used for in vitro transcription. In a typical reaction, ten micrograms of the cRNA was fragmented in the standard fragmentation buffer (40 mM Tris-acetate, 30 mM magnesium acetate, 100 mM potassium acetate) and dephosphorylated with Shrimp Alkaline Phosphatase (Amersham Biosciences, Piscataway, N.J.) at a final concentration of 0.01 U/ul. The Shrimp Alkaline Phosphatase was then heat inactivated at 65° C. for 15 minutes, and the reactions were purified by ethanol precipitation. The fragmented cRNA was placed into a ligation reaction containing 100 uM 3'biotin-CMP with 2 U/ul T4 RNA Ligase (New England Biolabs, Beverly, Mass.) and 16% PEG in the recommended buffer for 2 hours at 37° C. The ligation reaction was then added to a hybridization cocktail containing 0.5 mg/ml Acetylated BSA (Invitrogen Life Technologies, Carlsbad, Calif.), 0.1 mg/ml Herring Sperm DNA (Promega, Madison, Wis.), 50 pM Oligo B2 (Affymetrix Inc., Santa Clara, Calif.) and 1× Eukaryotic Hybridization Controls (Affymetrix Inc.), making up a total volume of 220 ul. 200 ul labeled cRNA target were hybridized to Affymetrix HuU95Av2 arrays for 16 hours at 45° C. Standard wash and stain protocols were used as recommended in the GeneChip Expression Analysis technical manual. Analyses were carried out using Affymetrix Microarray Suite Version 4.0.

FIG. 1 shows the percent present calls and average-average difference of end-labeled RNA and internally-labeled RNA. The average-average difference is the intensity of the perfect match probe minus the intensity of the mis-match probe averaged over all probe sets on the microarray and is a measure of the overall signal intensity. The percent present call is an output of the MicroArray Suite (Affymetrix, Inc., Santa Clara, Calif.) software based on gene probe set intensities. Both are considered metrics for labeling efficiency and RNA integrity. A greater number of genes are called present using the ligation method than using internally-labeled RNA. Furthermore, the fluorescent signal (as measured by the average average difference) is higher for the ligation method.

To test the reproducibility of the ligation labeling method, four independent reactions were carried through starting from total human heart RNA using the recommended GeneChip (Affymetrix, Inc., Santa Clara, Calif.) expression protocols, except that unlabeled ribonucleotides were used for in vitro transcription. Forty-five ug of the resulting cRNA were fragmented and treated with Shrimp Alkaline Phosphatase at a final concentration of 0.01 U/ul in duplicate 51 ul reactions at 37° C. for 1 hr. The Shrimp Alkaline Phosphatase was then heat inactivated at 65° C. for 15 minutes, and the reactions were purified by ethanol precipitation. 11 ug fragmented, dephosphorylated cRNA were ligated to 100 uM 3'biotin-CMP with 2 U/ul T4 RNA Ligase and 16% PEG for 2 hours at 37° C. in duplicate 33 ul reactions. Each 33 ul ligation reaction was then added to a hybridization cocktail containing 0.5 mg/ml Acetylated BSA (Invitrogen Life Technologies), 0.1 mg/ml Herring Sperm DNA, 50 pM Oligo B2 and 1× Eukaryotic Hybridization Controls, making up a total volume of 220 ul. 200 ul labeled cRNA target were hybridized to HuU95Av2 arrays (Affymetrix, Inc., Santa Clara, Calif.)

for 16 hours at 45° C. Standard wash and stain protocols were used as recommended in the GeneChip Expression Analysis technical manual (Affymetrix, Inc. Santa Clara, Calif.). Analyses were carried out using Microarray Suite Version 4.0 (Affymetrix, Inc. Santa Clara, Calif.).

A quantitative comparison of the expression data from the replicate reactions produces a correlation coefficient ($R^2$) of 0.98-0.99 between the replicates, underscoring the high reproducibility of the end-labeling method. Comparing the end-labeled replicates to internally-labeled RNA produces an $R^2$ value between 0.88-0.94.

EXAMPLE 4

Table 1 summarizes nucleic acid labeling reagents of the present invention (which are also described in greater detail above) and also provides convenient abbreviations (RLR=RNA Labeling Reagent):

TABLE 1

RNA labeling reagents

| Nomenclature | Compound |
| --- | --- |
| RLR-4a/pApB | 5'-pAp-TEG-biotin-3' |
| RLR-4b/pA$_5$pB | 5'-pA$_5$p-TEG-biotin-3' |
| RLR-5/pCpB | 5'-pCp-TEG-biotin-3' |
| RLR-6/AppCpB | A(5')pp(5')Cp-TEG-biotin-3' |
| RLR-7/pCpB$_5$ | 5'-pCp-(HEG-TEG-biotin)$_5$-3' |
| RLR-8/pCpB$_2$ | 5'-pCp-((HEG-TEG-biotin)$_2$-3' |
| RLR-9/pCpB$_3$ | 5'-pCp-((HEG-TEG-biotin)$_3$-3' |

EXAMPLE 5

Ligation Efficiency of RLR-4a and RLR-4b

The goal of these experiments was to demonstrate the concept of ligation-mediated labeling and determine the labeling efficiency of two different RNA Labeling Reagents (RLRs): RLR-4a, (5'pAp-TEG-biotin-3') and RLR-4b, (5'-pA$_5$p-TEG-biotin-3') [10]. RLR concentration (1 uM to 250 uM) and T4 RNA Ligase concentration (1 U/ul to 4 U/ul) were tested as well as ligation time (4 hr. and 8 hr). One reaction without T4 RNA Ligase served as a negative control. Another ligation reaction omitted the cRNA dephosphorylation step in order to test the requirement for dephosphorylation. All the reactions were performed with human heart RNA (Ambion) and were hybridized to Human U95Av2 arrays under standard conditions (10 ug labeled cRNA hybridized for 16 hours in 1× hybridization solution [100 mM MES, 1M Na+, 20 mM EDTA, 0.01% Tween20] at 45° C., 60 rpm). The arrays were washed, stained (using single stain protocol), and scanned according to the standard Affymetrix protocols.

The following concentrations were tested for each RLR compound: 50 uM, 10 uM, and 1 uM. Ligation took place for 4 hours at 30° C. with 2 U/ul T4 RNA Ligase (New England Biolabs). One RELA sample was not treated with Shrimp Alkaline Phosphatase and ligated with RLR-4a at 50 uM for comparison.

Both the signal (AvgAvgDifference) and the present call rate (% P) were improved by increasing RLR concentration and T4 RNA Ligase concentration independently. The best performance was achieved by increasing RLR concentration in conjunction with enzyme concentration. The mononucleotide RLR-4a consistently performed better than pentanucleotide RLR-4b, the five-mer, at the same concentrations. No significant difference was observed between a 4 hour incubation and an 8 hour incubation. Dephosphorylation of the cRNA is necessary for efficient ligation, as demonstrated by the low signal and number of present calls in the "50 uM RLR-4a non-SAP treated sample. Background intensity was comparable across all the arrays. At this stage, the optimum reaction conditions were 250 uM RLR-4a, 4 U/ul T4 RNA Ligase for 4 hours at 30° C. These experiments demonstrate the viability of end-labeling RNA for use with DNA microarrays.

EXAMPLE 6

Ligation Efficiency of RLR-5

We next tested a range of RLR-5 (5'-pCp-TEG-biotin-3') concentrations in the ligation reaction. In the literature, 5'-[$^{32}$P]pCp-3' is putatively the preferred donor molecule under most radio-labeling conditions [5]. We tested the following range of RLR-5 concentrations at 20° C.: 50 uM, 100 uM, 250 uM, 500 uM and 1000 uM. In addition, two 250 uM RLR-5 reactions were incubated at 30° C. and 37° C. for comparison to the 20° C. reaction temperature. The ligation reactions were carried out using human heart RNA, 2 U/ul T4 RNA Ligase and 16% PEG for 2 hours.

All of the RLR-5 samples gave equivalent or better signals compared to the standard. The 100 uM RLR-5 sample gave the highest signal, but this difference may be within experimental error. There was no significant difference in signal between the 20° C., 30° C. and 37° C. incubation temperatures of the 250 uM RLR-5 sample. However, the 37° C. incubation of 250 uM RLR-5 gave the best overall present call rate of all the conditions tested. RLR-5 concentrations between 50 uM-250 uM gave equivalent or better present call rates compared to the standard; RLR-5 concentrations greater than or equal to 500 uM may be slightly inhibitory as demonstrated by the slightly lower present calls, although signal intensity remained high. These experiments demonstrate that RLR-5 slightly outperforms RLR-4a: at 50 uM RLR concentration, 16% PEG and 20° C., RLR-5 has slightly higher signal and present calls than RLR-4a (50 uM RLR-4a, 16% PEG, 20° C.: 32.0% P, 104 unscaled signal; 93 scaled signal).

The $R^2$ correlation between the standard method and RELA method ranged from 0.93-0.94. The $R^2$ correlation between different ligation reactions ranged from 0.97-0.99, which is comparable to the variance of the standard labeling method.

EXAMPLE 7

Ligation Efficiency of RLR-6

In this experiment, we tested the performance of RLR-6 (A(5')pp(5')Cp-TEG-biotin-3') the adenylated donor intermediate, at different concentrations in the ligation reaction. We also measured the kinetics of the reaction, comparing the effect of ligation time, RLR concentration, and enzyme concentration on array performance. The following seven reactions were carried out using human heart RNA on U95Av2 arrays:

| | | |
| --- | --- | --- |
| 1) Standard (internally-labeled cRNA) | | |
| 2) 50 uM RLR-6 | 20 min. | 2.0 U/ul T4 RNA Ligase |
| 3) 100 uM RLR-6 | 20 min. | 2.0 U/ul T4 RNA Ligase |
| 4) 200 uM RLR-6 | 20 min. | 2.0 U/ul T4 RNA Ligase |
| 5) 100 uM RLR-6 | 5 min. | 2.0 U/ul T4 RNA Ligase |
| 6) 100 uM RLR-6 | 120 min. | 2.0 U/ul T4 RNA Ligase |
| 7) 100 uM RLR-6 | 20 min. | 0.5 U/ul T4 RNA Ligase |

After only 20 minutes, the 100 uM and 200 uM concentrations of RLR-6 with 2 U/ul T4 RNA Ligase gave equivalent or better signal compared to the standard. Signal increases as the reaction time is increased from 5 minutes to 20 minutes to 120 minutes in the 100 uM RLR-6 reaction. Similarly, signal increases as RLR-6 concentration increases from 50 uM to 100 uM to 200 uM with the 20 minute ligation time. The highest signal was achieved with the 100 uM RLR-6, 2 U/ul T4 RNA Ligase, 120 minute reaction; the signal correlated well with that of the standard, with an $R^2$ correlation of 0.93. The next highest signal was achieved with the 200 uM, 20 minute ligation, which had an $R^2$ correlation of 0.94 compared to the standard.

In terms of enzyme concentration, using 0.5 U/ul T4 RNA Ligase, or one-quarter of the normal amount, reduced the signal by half. The present call results followed the same trend as the signal results. With the exception of the 5 minute reaction and 0.5 U/ul Ligase reaction, all of the reactions resulted in an equivalent or better number of present calls compared to the standard. The condition that gave the best overall result was the 100 uM RLR-6, 2 U/ul T4 RNA Ligase, 2 hr. reaction. The next best result came from the 200 uM, 20 minute reaction, which had comparable present calls but slightly slower signal.

We also tested the need for ATP in the ligation reaction with RLR-6. Because RLR6 is a pre-adenylated donor molecule, ATP should not be necessary in the ligation reaction and could possibly be inhibitory [7]. Indeed, the above reactions were performed without ATP, demonstrating that ATP is not necessary for efficient ligation with RLR-6. We found that the presence of ATP does have a slight inhibitory effect.

EXAMPLE 8

Ligation Reaction Additives

In this experiment we sought to increase ligation efficiency by adding substances known to enhance various enzymatic reactions involving nucleic acids. Reports in the literature suggest that additives, such as BSA, DMSO and PEG can improve the ligation efficiency for some substrates [11, 12]. Starting from fragmented, dephosphorylated human heart cRNA, we tested ligation with the following additives: 1) 10 ug/ml BSA, 2) 10% DMSO, 3) 16% PEG 8000, 4) no additive (control). The four reactions were carried out with 2 U/ul T4 RNA Ligase (from NEB) and 50 uM RLR-4a (suboptimal ligation conditions). A fifth ligation reaction using Promega T4 RNA Ligase without additives was included for a vendor comparison. The ligation reactions were hybridized to U95Av2 arrays under standard conditions.

Of the three additives only PEG had a significant effect on ligation efficiency in terms of array performance. The addition of 16% PEG dramatically increased overall signal intensity and present call percentage compared to the no additive control. BSA appeared to hinder ligation, as demonstrated by the lower signal intensity and lower present call rate. The DMSO did not have an effect on signal or present call rate. In terms of enzyme performance, the NEB T4 RNA Ligase was much more effective than the Promega version, which had the lowest signal and present call rate of all the conditions tested.

We set out to identify the optimal PEG concentration in the ligation reaction. As with the previous optimization experiments, we tested ligation under suboptimal conditions in order to discern subtle differences between the different conditions tested. The ligation reactions were carried out with 2 U/ul T4 RNA Ligase and 50 uM RLR-4a at 20° C. for 2 hr. with the following concentrations of PEG: 0%, 10%, 16%, and 25%. We also tested a higher concentration of RLR-4a, 179 uM, plus or minus 16% PEG. The ligations were hybridized to U95Av2 arrays under standard conditions.

Increasing the PEG concentration in the ligation reaction increased both the signal and the present call percentage. Within the 50 uM RLR-4a subset, the best signal was achieved with the 25% PEG ligation reaction. In terms of present calls, the 16% PEG and 25% PEG ligations gave equivalent results, exceeding the present call percentage of the standard by ~2%. The addition of PEG proved beneficial even at the highest RLR-4a concentration tested, 179 uM. The addition of 16% PEG increased the signal by 1.3 fold and the present calls by almost 6% in comparison to the "no PEG" control. Due to the high viscosity of the PEG solution, we have found that a final concentration of 16% PEG enhances array performance and is methodologically tractable.

EXAMPLE 9

RNA Fragmentation

Testing $Mg^{2+}$ Hydrolysis Parameters

In order to optimize array performance, we examined different fragmentation buffers and the effect of fragment length on array performance. For the RELA method we tested the relationship between fragment length, array intensity and detection sensitivity.

Because the downstream ligation reaction is affected by the fragmentation buffer, we examined buffers with lower monovalent ion concentrations and alternative cation compositions. Labeled and unlabeled cRNA was prepared from HeLa total RNA following standard expression protocols. Both labeled and unlabeled cRNAs were fragmented using $Mg^{2+}$ and high heat in the following buffers: a) 5×=200 mM Tris-acetate, pH 8.1, 150 mM MgOAc, 500 mM KOAc (Affymetrix standard) b) 5×=200 mM Tris, 150 mM MgOAc, pH 8.2 c) 5×=200 mM Tris, 150 mM MgCl2, pH 8.2. The fragmented unlabeled cRNA was dephosphorylated with Shrimp Alkaline Phosphatase at 37° C. for 1 hour; followed by heat-inactivation at 65° C. for 15 minutes. The dephosphorylated, fragmented cRNA was end-labeled with 100 uM RLR-6 at 37° C. for 2 hours in a reaction containing 2 U/ul T4 RNA Ligase, 16% PEG. For all reactions, ten micrograms of labeled cRNA were hybridized to U133A arrays and processed according to the standard antibody amplification protocol.

For both RELA and STD, MgOAc was preferred over $MgCl_2$ for the highest overall signal intensities and number of present calls. The standard cRNA fragmented with the Affymetrix commercial buffer performed the best by far. Fragmentation of the standard cRNA with the modified buffers significantly reduced both the number of present calls and signal intensity. For the RELA samples, the present call rates did not vary significantly between the different fragmentation buffers tested. However, the RELA samples fragmented with MgOAc containing buffers had higher signals than the sample which was fragmented with the $MgCl_2$ buffer.

EXAMPLE 10

End-labeling with Multiple Biotins

RLR-7, RLR-8 and RLR-9

In accordance with one aspect of the present invention, the Sig moiety may have multiple biotin residues. In accordance with the present invention, it has been discovered that use of a nucleic acid labeling compound having multiple biotin residues to end label RNA has the potential of increasing target RNA signal as well as detection sensitivity. However, preliminary data indicates that there are limits to the number of biotin residues which can be incorporated into a Sig moiety and usefully employed to end label RNA for purposes of detection as described in accordance with the present invention.

In regards to possible limits to the number of biotin moieties which may usefully be incorporated into a donor molecule, a donor molecule with five TEG-biotins attached to the 3' position of the ribose (5'-pCp-(TEG-biotin)$_5$-3'), called RLR-7 was synthesized. In preliminary experiments, RNA was labeled with RLR-7 and hybridized to a GeneChip® array gave and in this experiment aberrant hybridization results. The overall hybridization pattern of RNA labeled with RLR-7 is somewhat similar to those of the standard and of RLR-5, having one biotin. In many cases, however, RLR-7 hybridization missed areas where signal should be present and lit up areas which are not present in the standard. The significance, if any, of this preliminary data with RLR-7 is unknown at the present time.

Donor molecules having less than five biotin moieties were prepared: RLR-8 (2 biotins), and RLR-9 (3 biotins). RLR-9 gave the highest unscaled signal intensity. However, background intensity increases proportionately as signal increases. In the preliminary experiments performed, RLR-9 performed well compared to the other RNA labeling reagents being tested. Despite having the highest background, RLR-9 had the highest overall number of present calls compared to RLR-5 and RLR-8.

EXAMPLE 11

PEG Optimization

In this experiment, we set out to identify the optimal PEG concentration in the ligation reaction. As with the previous optimization experiments, we tested ligation under suboptimal conditions in order to discern subtle differences between the different conditions tested. The ligation reactions were carried out with 2 U/ul T4 RNA Ligase and 50 uM RLR-4a at 20° C. for 2 hr. with the following concentrations of PEG: 0%, 10%, 16%, and 25%. We also tested a higher concentration of RLR-4a, 179 uM, plus or minus 16% PEG. The ligations were hybridized to U95Av2 arrays under standard conditions.

Increasing the PEG concentration in the ligation reaction increased both the signal and the present call percentage. Within the 50 uM RLR-4a subset, the best signal was achieved with the 25% PEG ligation reaction. In terms of present calls, the 16% PEG and 25% PEG ligations gave equivalent results, exceeding the present call percentage of the standard by ~2%. The addition of PEG proved beneficial even at the highest RLR-4a concentration tested, 179 uM. The addition of 16% PEG increased the signal by 1.3 fold and the present calls by almost 6% in comparison to the "no PEG" control. Due to the high viscosity of the PEG solution, we have found that a final concentration of 16% PEG enhances array performance and is methodologically tractable.

EXAMPLE 12

Array Performance of RNase III Fragmented cRNA

In this experiment, we tested two different methods of RNA fragmentation within the RELA protocol (RNA End Labeling Analysis) for comparison to the standard method. Previously, gel shift assays revealed that $Mg^{2+}$-hydrolyzed RNA is not efficiently ligated using T4 RNA Ligase. Therefore, we turned to an alternative fragmentation method using RNase III for digestion. We digested the RNA with 1 unit of enzyme per 10 micrograms of cRNA at 37° C. for 35; the RNase III enzyme is then heat-inactivated at 65° C. for 20 minutes. Next, the fragmented RNA is dephosphorylated using Shrimp Alkaline Phosphatase and ligated to RLR-5 with T4 RNA Ligase.

|  | Samples (duplicate): | Hyb Temp |
|---|---|---|
| RELA | 1) Standard | 45° C. |
| | 2) Mg fragmentation | 50° C. |
| | 3) RNase → SAP | 45° C. |
| | 4) RNase → SAP | 50° C. |
| | 5) [RNase + SAP] | 45° C. |
| | 6) [RNase + SAP] | 50° C. |
| | 7) [RNase + SAP] 40' | 50° C. |

For three reactions, we tested combining the RNase digestion and dephosphorylation steps to reduce the length of the assay. From now on, we will refer to these reactions as "two-step" reactions since the RELA protocol is essentially reduced into two steps: 1) Fragmentation & dephosphorylation, 2) Ligation. For these reactions, fragmentation and dephosphorylation took place simultaneously for 35 or 40 minutes, followed by a heat-inactivation of both enzymes at 65° C. for 20 minutes. Several targets were hybridized at 50° C. based on previous findings that this higher temperature improves discrimination. All reactions were performed in duplicate and hybridized to U133A arrays according to standard protocols.

RNase fragmentation significantly improves signal intensity. Within the RELA protocol, RNase digestion improves intensity by a factor of 2 fold over $Mg^{2+}$-hydrolyzed cRNA. This is consistent with the gel shift results which indicate that RNase-digested RNA is more efficiently ligated than $Mg^{2+}$-hydrolyzedRNA. Compared to the standard protocol, RNase fragmentation increases signal by approximately 1.2 fold. Hybridization of the RNase-digested targets at 50° C. vs. 45° C. lowered signal intensity by 5-10%, but these signals were still higher than those of the standards which were hybridized at 45° C. The two-step reactions performed as well as those prepared using standard version of the RELA protocol, with signals >=240.

PARTIAL LIST OF REFERENCES REFERRED TO ABOVE

1. England T E, Uhlenbeck O C: 3'-terminal labelling of RNA with T4 RNA ligase. *Nature* 1978, 275:560-561.
2. Richardson R W, Gumport R I: Biotin and fluorescent labeling of RNA using T4 RNA ligase. *Nucleic Acids Research (Online)* 1983, 11:6167-6184.
3. Silber R, Malathi V G, Hurwitz J: Purification and properties of bacteriophage T4-induced RNA ligase. *Proceedings of the National Academy of Sciences of the United States of America* 1972, 69:3009-3013.
4. Kaufmann G, Klein T, Littauer U Z: T4 RNA ligase: substrate chain length requirements. *Febs Letters* 1974, 46:271-275.
5. Romaniuk E, McLaughlin L W, Neilson T, Romaniuk P J: The effect of acceptor oligoribonucleotide sequence on the T4 RNA ligase reaction. *European Journal of Biochemistry* 1982, 125:639-643.
6. Atencia E A, Madrid O, Gunther Sillero M A, Sillero A: T4 RNA ligase catalyzes the synthesis of dinucleoside polyphosphates. *European Journal of Biochemistry* 1999, 261: 802-811.
7. McLaughlin L W, Piel N, Graeser E: Donor activation in the T4 RNA ligase reaction. *Biochemistry* 1985, 24:267-273.
8. Hoffmann P U, McLaughlin L W: Synthesis and reactivity of intermediates formed in the T4 RNA ligase reaction. *Nucleic Acids Research (Online)* 1987, 15:5289-5303.
9. Uhlenbeck O C, Cameron V: Equimolar addition of oligoribonucleotides with T4 RNA ligase. *Nucleic Acids Research (Online)* 1977, 4:85-98.
10. England T E, Uhlenbeck O C: Enzymatic oligoribonucleotide synthesis with T4 RNA ligase. *Biochemistry* 1978, 17:2069-2076.
11. Tessier D C, Brousseau R, Vernet T: Ligation of single-stranded oligodeoxyribonucleotides by T4 RNA ligase. *Analytical Biochemistry* 1986, 158:171-178.
12. Harrison B, Zimmerman S B: Polymer-stimulated ligation: enhanced ligation of oligo- and polynucleotides by T4 RNA ligase in polymer solutions. *Nucleic Acids Research (Online)* 1984, 12:8235-8251.

13. Eun H-M: *Enzymology Primer for Recombinant DNA Technology*. San Diego: Academic Press; 1996.
14. Golub T R, Slonim D K, Tamayo P, Huard C, Gaasenbeek M, Mesirov J P, Coller H, Loh M L, Downing J R, Caligiuri M A, Bloomfield C D, Lander E S: Molecular classification of cancer: class discovery and class prediction by gene expression monitoring. *Science* 1999, 286:531-537.
15. Armstrong S A, Staunton J E, Silverman L B, Pieters R, den Boer M L, Minden M D, Sallan S E, Lander E S, Golub T R, Korsmeyer S J: MLL translocations specify a distinct gene expression profile that distinguishes a unique leukemia. *Nature Genetics* 2002, 30:41-47.

The aforementioned references are hereby incorporated by reference.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by references for all purposes.

What is claimed is:

1. A method of detecting the presence of an RNA of interest, said method comprising the following steps,
   providing a sample comprising RNA which may or may not have said RNA of interest;
   ligating said RNA with a labeling reagent having the formula

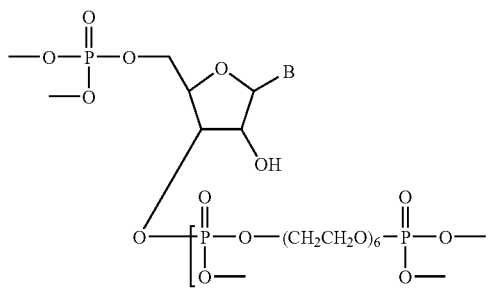

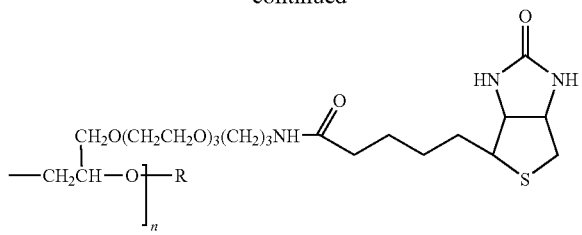

where B is a heterocyclic moiety; and R is selected from the group consisting of H and $PO_3^=$ and n is 1 to 6;
   providing a nucleic acid array with probes corresponding to said RNA of interest;
   hybridizing the labeled nucleic acid fragments to the nucleic acid array;
   and determining the extent of hybridization to said probes to determine the presence of said RNA of interest.

2. A method according to claim 1 wherein said RNA comprises microRNA.

3. A method according to claim 1 further comprising the steps of treating said sample with a fragmenting reagent to provide RNA fragments; and
   removing phosphate groups from said fragments to provide fragments with free 3' OH groups after said step of providing said sample and before said step of ligating.

4. A method according to claim 3 wherein said fragmenting agent is selected from the group consisting of RNAse III and a buffer containing a divalent metal ion and having a pH in the neutral to alkaline range.

5. A method according to claim 3 wherein said step of removing phosphate groups from 3' hydroxyl groups is carried out with alkaline phosphatase.

6. A method according to claim 1 wherein B is selected from the group consisting of adenine, guanine, cytosine, and uracil and n is 2 to 4.

7. A method according to claim 6 wherein B is selected from the group of adenine and cytosine.

8. A method according to claim 7 wherein B is cytosine.

9. A method according to claim 6 wherein n is 3.

10. A method according to claim 1 wherein said labeling reagent is

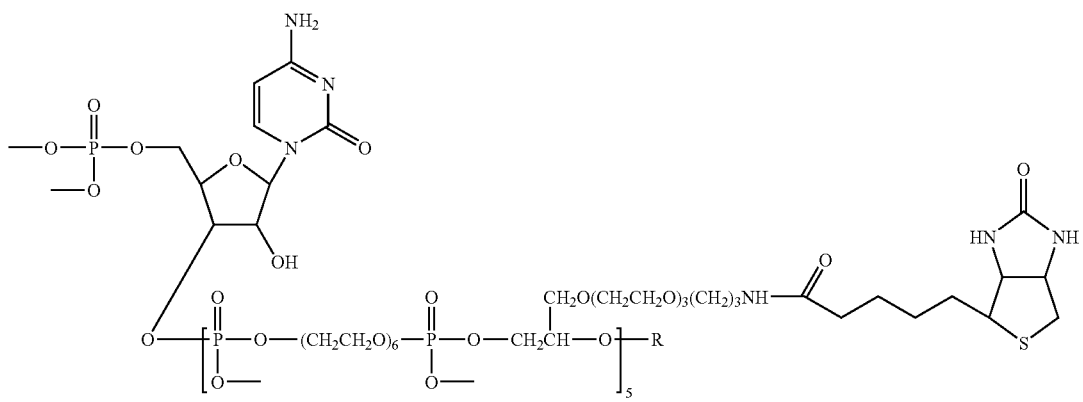

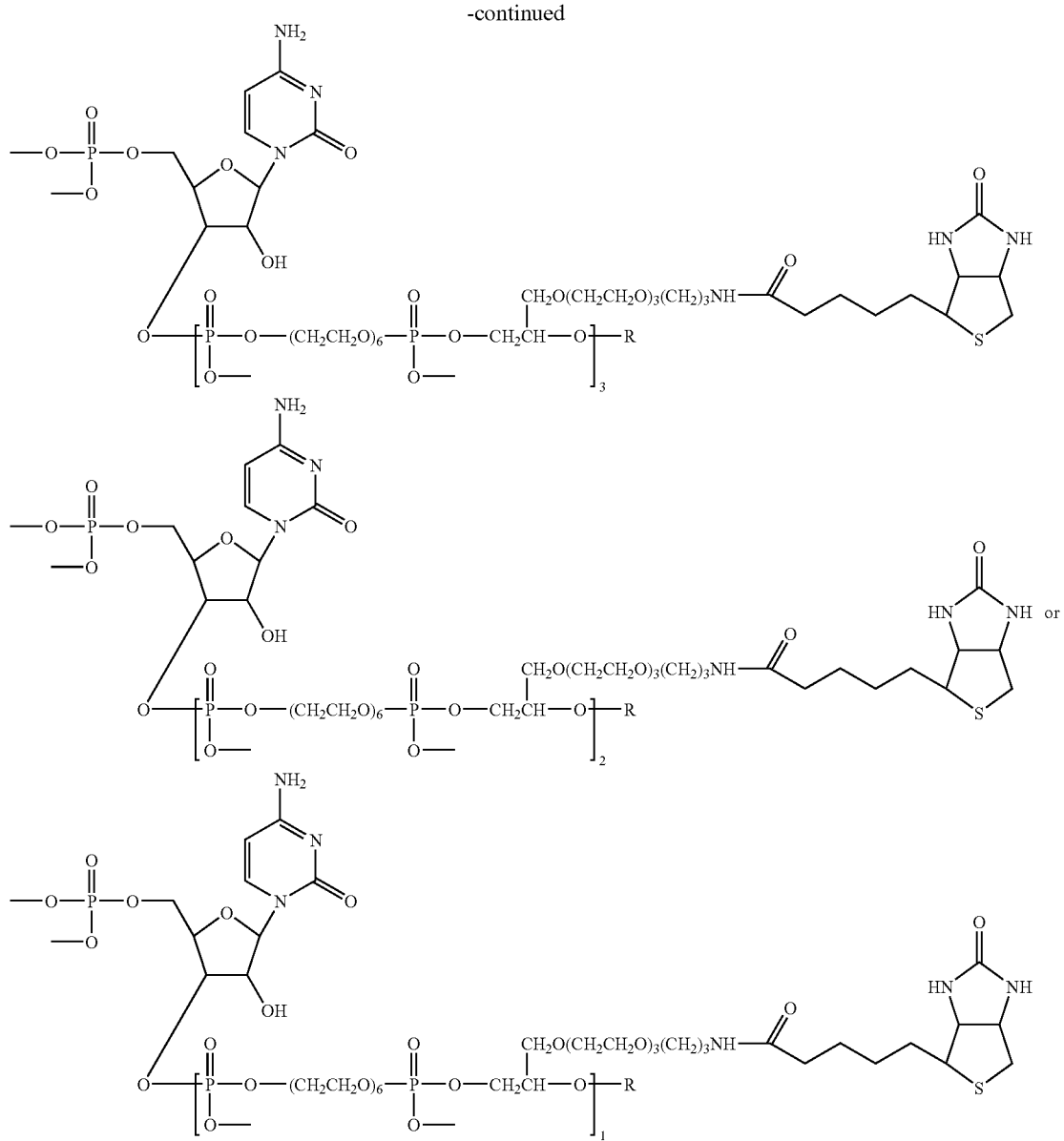

where R is H or $PO_3^{2-}$.

11. The method of claim 4 wherein the divalent metal ion is Mg2+.

12. A method according to claim 6 wherein said RNA comprises microRNA.

13. A method according to claim 6 further comprising the steps of:
    treating said sample with a fragmenting reagent to provide RNA fragments; and
    removing phosphate groups from said fragments to provide fragments with free 3' OH groups after said step of providing said sample and before said step of ligating.

14. A method according to claim 13 wherein said fragmenting agent is selected from the group consisting of RNAse III and a buffer containing a divalent metal ion and having a pH in the neutral to alkaline range.

15. The method of claim 14 wherein the divalent metal ion is Mg2+.

16. A method according to claim 13 wherein said step of removing phosphate groups from 3' hydroxyl groups is carried out with alkaline phosphatase.

* * * * *